US00PP13214P3

(12) United States Plant Patent
Vandenberg

(10) Patent No.: US PP13,214 P3
(45) Date of Patent: Nov. 12, 2002

(54) ROSE PLANT NAMED 'YOWIPI'

(75) Inventor: Cornelis P. Vandenberg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/821,999

(22) Filed: Mar. 31, 2001

(65) Prior Publication Data

US 2002/0144312 P1 Oct. 3, 2002

(51) Int. Cl.[7] ..... A01H 5/00

(52) U.S. Cl. ..... Plt./132

(58) Field of Search ..... Plt./132, 130, 133

*Primary Examiner*—Bruce R. Campell
*Assistant Examiner*—June Hwu
(74) *Attorney, Agent, or Firm*—C. A. Whealy

(57) ABSTRACT

A distinctive cultivar of Hybrid Tea Rose plant named 'Yowipi', characterized by its dark green leaves; long, thick and dark red stems; large white and pink flowers with ruffled petal margins; and good postproduction longevity.

1 Drawing Sheet

BOTANICAL CLASSIFICATION/CULTIVAR DESIGNATION

*Rosa hybrida* cultivar Yowipi.

BACKGROUND OF THE INVENTION

The present invention relates to a new and distinct cultivar of Hybrid Tea Rose plant, botanically known as *Rosa hybrida,* commercially produced as a cut flower, and hereinafter referred to by the name 'Yowipi'.

The new cultivar is a product of a planned breeding program conducted by the Inventor in Salinas, Calif. The objective of the breeding program was to develop new cut Rose cultivars with attractive flower petal colors, long and strong stems, dark green leaves and good postproduction longevity.

The new cultivar originated from a cross made by the Inventor in 1996 of an unnamed proprietary selection, as the female, or seed, parent with the cultivar Tango, not patented, as the male, or pollen, parent. The cultivar Yowipi was discovered and selected by the Inventor as a flowering plant within the progeny of the stated cross in a controlled environment in February, 1999, in Madrid, Cundinamarca, Colombia.

Since March, 2000, asexual reproduction of the new cultivar by grafting on *Rosa Manetti* rootstocks in Madrid, Cundinamarca, Colombia, has shown that the unique features of the new cultivar are stable and reproduced true to type in successive generations of asexual reproduction.

SUMMARY OF THE INVENTION

The following traits have been repeatedly observed and are determined to be the unique characteristics of 'Yowipi'. These characteristics in combination distinguish the new Hybrid Tea Rose as a new and distinct cultivar:

1. Dark green leaves.
2. Long, thick and dark red stems.
3. Large white and pink flowers with ruffled petal margins.
4. Good postproduction longevity.

Plants of the Hybrid Tea Rose can be compared to plants of the female parent, an unnamed proprietary selection. In side-by-side comparisons conducted by the Inventor in Salinas, Calif., plants of the new cultivar differed from plants of the unnamed proprietary selection in the following characteristics:

1. Flowering stems of the new Hybrid Tea Rose have more thorns than flowering stems of the unnamed proprietary selection.
2. Plants of the new Hybrid Tea Rose have white and pink-colored flower petals whereas plants of the unnamed proprietary selection have pink bi-colored flower petals.

Plants of the Hybrid Tea Rose can be compared to plants of the female parent, the cultivar Tango. In side-by-side comparisons conducted by the Inventor in Salinas, Calif., plants of the new cultivar differed from plants of the cultivar Tango in the following characteristics:

1. Plants of the new Hybrid Tea Rose have much longer flowering stems than plants of the cultivar Tango.
2. Flowering stems of the new Hybrid Tea Rose have more thorns than flowering stems of the cultivar Tango
3. Plants of the new Hybrid Tea Rose have larger flowers than plants of the cultivar Tango.
4. Plants of the new Hybrid Tea Rose have white and pink-colored flower petals whereas plants of the cultivar Tango have white and orange-colored flower petals.

Plants of the new Hybrid Tea Rose have not been observed under all possible environmental conditions. The phenotype may vary significantly with variations in environment such as temperature, light, water status and/or fertilizer type and rate, without, however, any variance in genotype.

BRIEF DESCRIPTION OF PHOTOGRAPH

The accompanying colored photograph illustrates the new Hybrid Tea Rose plant, showing the colors as true as it is reasonably possible to obtain in colored reproductions of this type. Colors in the photograph may differ slightly from the color values cited in the detailed botanical description which accurately describe the colors of the new Hybrid Tea Rose.

The photograph comprises a side perspective view of a typical flowering stem of the new Hybrid Tea Rose grown in Madrid, Cundinamarca, Colombia.

DETAILED BOTANICAL DESCRIPTION

The following observations and measurements describe cut flowering stems of plants grown in Madrid, Cundinamarca, Colombia, in polyethylene-covered greenhouses with day temperatures ranging from 14 to 20° C., night temperatures ranging from 4 to 8° C., and light levels ranging from 3,000 to 5,000 foot-candles. Flowering stems used in the photograph and the description were about 75 days old. In the following description, color references are made to The Royal Horticultural Society Colour Chart except where general terms of ordinary dictionary significance are used.

Classification:

*Botanical.*—*Rosa hybrida* cultivar Yowipi.

*Commercial.*—Hybrid Tea Rose used as a cut flower.

Parentage:

*Female, or seed, parent.*—Unnamed *Rosa hybrida* proprietary selection, not patented.

*Male, or pollen, parent.*—*Rosa hybrida* cultivar Tango, not patented.

Propagation:

*Type.*—Cuttings grafted onto *Rosa Manetti* rootstocks.

Plant description:

*Form.*—Upright; narrow.

*Growth habit.*—Moderately vigorous.

*Plant height.*—About 86 to 97 cm.

*Plant width.*—About 21 cm.

*Stem and lateral branches (peduncles).*—Lateral branch length: About 86 to 97 cm. Lateral branch diameter: Base: Thick, about 9 mm. Apex: Thick, about 5 mm. Internode length: About 4.6 cm. Texture: Smooth. Strength: Strong. Color: Young: 146A overlain with 187A. Mature: Close to 187A. Thorns: Quantity: About 2 per 12 cm of stem. Height: About 8 mm. Width at base: About 8 mm. Shape: Deltoid. Color, immature and mature: 59A.

*Foliage description.*—Arrangement: Alternate, compound with typically three to five leaflets per leaf. Leaf length, five-leaflet leaves: Terminal leaves: About 7.7 cm. Lateral leaves: About 6.5 cm. Leaf width, five-leaflet leaves: Terminal leaves: About 5.5 cm. Lateral leaves: About 4.7 cm. Leaflet shape: Ovate. Leaflet apex: Acuminate. Leaflet base: Obtuse. Leaflet margin: Sharply serrate. Leaflet texture: Smooth, leathery, glabrous. Occasional small thorns on lower petiole and midrib of terminal leaflet, about 1 by 1 mm in size and close to 146A in color. Petiole length, 5-leaflet leaves: About 9.5 cm. Petiole diameter: At stem attachment: About 6.5 mm. At base of terminal leaves: About 1.75 mm. Stipules: Quantity: Two at base of petiole. Length: About 1.7 cm. Length of appendages: About 6 mm. Width: About 1 mm. Color: Young and mature foliage, upper surface: 147A; venation, 147A to 147B. Young and mature foliage, lower surface: 147B; venation, 147C. Petiole: Upper surface: Close to 59A. Lower surface: 146A; nodes, close to 59A. Stipules, upper surface: 147A. Stipules, lower surface: 147B.

Flower description:

*Flower type and habit.*—Large white and pink flowers. Consistently symmetrical rosette flowers. Freely and recurrent flowering. Flowers arranged singly at terminal apices. Flowers persistent.

*Flowering season/time to flower.*—Year-round under greenhouse conditions. Depending on environmental conditions and season, time to flower is about 76 days.

*Flower diameter, fully opened.*—About 13.5 cm.

*Flower depth (height), fully opened.*—About 5.7 cm.

*Flower longevity as a cut flower.*—At least 8 to 10 days.

*Fragrance.*—Strong, typical Hybrid Tea Rose fragrance.

*Flower buds.*—Shape: Ovoid. Length: About 5.1 cm. Color: 144A.

*Petals and petaloids.*—Petaloids vary in size, but similar to petals in shape and coloration. Quantity: About 33. Length, outer petals: About 7.3 cm. Width, outer petals: About 8 cm. Shape: Broadly obovate. Apex: Rounded. Base: Obtuse. Margin: Entire, undulate and ruffled. Texture: Smooth, satiny. Color: When opening, upper surface: White, close to 155A, overlain with pink, 68A; more pink towards apex and mostly white, close to 155A, towards base. When opening, lower surface: White, close to 155A, overlain with pink, 68A to 68B; more pink towards apex and mostly white, close to 155A, towards base. Fully opened, upper surface: White, close to 155A, overlain with pink, 68A to 68B to 62A; more pink towards apex and mostly white, close to 155A, towards base; color does not fade with subsequent development. Fully opened, lower surface: White, close to 155A, overlain with pink, 68B to 62A; more pink towards apex and mostly white, close to 155A, towards base.

*Sepals.*—Quantity: Five. Length: About 4.5 cm. Diameter: About 1.2 cm. Shape: Sharply lanceolate. Apex: Elongated, acuminate. Base: Fused at receptacle. Margin: Ciliate with occasional sharply acuminate appendages. Texture: Upper surface, pubescent; lower surface, slightly pubescent. Color: Upper surface: Closest to 144B. Lower surface: 144A with central longitudinal stripe, 59A.

*Reproductive organs.*—Stamens: Quantity: About 118 per flower. Anther length: About 3 mm. Anther diameter: About 2 mm. Anther shape: Cordate, concave. Anther color: Close to 14A. Filament length: About 3 mm. Filament color: Close to 7A. Pollen amount: None. Pistils: Quantity: About 73 per flower. Pistil length: About 9 mm. Style color: Close to 45A. Stigma shape: Bi-lobed. Stigma color: Close to 5D. Ovary color: 145D to 155D. Receptacle height: About 1.1 cm. Receptacle diameter: About 1.1 cm. Receptacle texture: Smooth. Receptacle color: 144A.

*Seed.*—None observed.

Disease resistance: Plants of the new Hybrid Tea Rose have been observed to be somewhat resistant to Powdery Mildew.

It is claimed:

1. A new and distinct Hybrid Tea Rose plant named 'Yowipi', as illustrated and described.

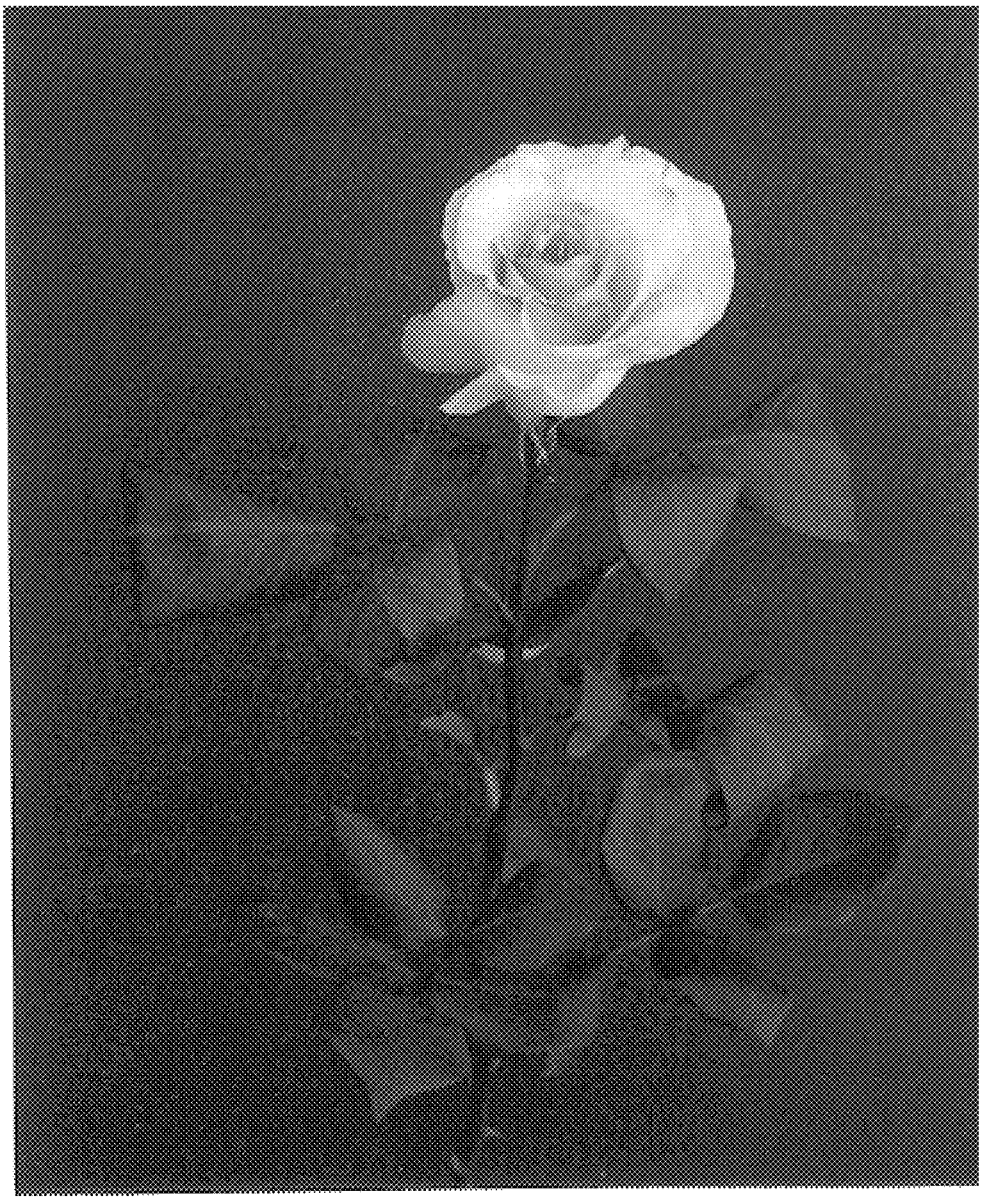

* * * * *